United States Patent
Wender et al.

(10) Patent No.: US 10,401,345 B2
(45) Date of Patent: *Sep. 3, 2019

(54) AUTO MICRONAIRE

(71) Applicant: Uster Technologies AG, Uster (CH)

(72) Inventors: James T. Wender, Seymour, TN (US); Youe-Tsyr Chu, Knoxville, TN (US); Hossein M. Ghorashi, Knoxville, TN (US); Michael E. Galyon, Knoxville, TN (US)

(73) Assignee: Uster Technologies, AG, Uster (CH)

( * ) Notice: Subject to any disclaimer, the term of this patent is extended or adjusted under 35 U.S.C. 154(b) by 131 days.

This patent is subject to a terminal disclaimer.

(21) Appl. No.: 15/083,335

(22) Filed: Mar. 29, 2016

(65) Prior Publication Data

US 2016/0209392 A1 Jul. 21, 2016

Related U.S. Application Data (63) Continuation of application No. 13/592,447, filed on Aug. 23, 2012, now Pat. No. 9,329,162.

(60) Provisional application No. 61/596,284, filed on Feb. 8, 2012.

(51) Int. Cl.
*G01N 33/36* (2006.01)
*G01N 21/89* (2006.01)

(52) U.S. Cl.
CPC ......... *G01N 33/362* (2013.01); *G01N 33/365* (2013.01); *G01N 21/8915* (2013.01)

(58) Field of Classification Search
CPC ............. G01N 33/362; G01N 21/8915; G01N 33/365; D01G 99/00

USPC .................................................... 73/159, 160
See application file for complete search history.

(56) References Cited

U.S. PATENT DOCUMENTS

| | | | |
|---|---|---|---|
| 5,270,787 A | 12/1993 | Shofner et al. | |
| 5,367,747 A * | 11/1994 | Shofner | D01G 99/00 19/65 R |
| 5,483,844 A | 1/1996 | Shofner et al. | |
| 5,892,142 A | 4/1999 | Gorashi et al. | |
| 6,085,584 A | 7/2000 | Ramachandran et al. | |
| 6,397,437 B1 * | 6/2002 | Shofner | D01G 31/006 19/66 CC |
| 7,143,642 B1 | 12/2006 | Baxter et al. | |
| 9,891,145 B1 * | 2/2018 | Mansfield | G01N 33/362 |
| 2006/0179932 A1 | 8/2006 | Ramachandran et al. | |
| 2008/0236252 A1 | 10/2008 | Wender et al. | |
| 2017/0122924 A1 * | 5/2017 | Righettini | G01N 19/00 |

FOREIGN PATENT DOCUMENTS

| | | | | |
|---|---|---|---|---|
| CN | 202075215 | * | 12/2011 | ............. G01N 21/00 |
| WO | WO-9940427 A1 | * | 8/1999 | ........... G01N 33/362 |

* cited by examiner

*Primary Examiner* — Benjamin R Schmitt
(74) *Attorney, Agent, or Firm* — Luedeka Neely Group, P.C.; Rick Barnes (57) ABSTRACT

A fiber testing instrument having a fiber loading station that is sized to accommodate a fiber sample within a desired size range, a fiber extraction device for extracting a portion of the fiber sample for a first battery of fiber tests, a fiber transport device for conveying at least the remaining portion of the fiber sample, and a micronaire chamber for receiving the conveyed fiber sample, where the micronaire chamber is sized to test any fiber sample within the desired size range.

7 Claims, 12 Drawing Sheets

AUTO MICRONAIRE

FIELD

This patent application claims all rights and priority on prior pending U.S. patent application Ser. No. 13/592,447 filed Aug. 23, 2012 and thereby to provisional patent application Ser. No. 61/596,284 filed Feb. 8, 2012. This invention relates to the field of fiber measurement. More particularly, this invention relates to utilizing a single fiber sample for multiple measurements on multiple instruments.

INTRODUCTION

Fiber processors, manufacturers, sellers, and buyers perform multiple tests upon the fibers at various stages, so as to know the value of the fibers, how to process the fibers, and other important properties of the fibers. For example, in the cotton fiber industry, properties of the cotton fibers such as micronaire, length, strength, color, moisture content, and trash content are all important properties to measure and know at various stages of processing and sale.

Typically, each test requires that a separate sample be taken from the fiber source (such as a bundle or a flow), the individual test performed, and then the sample either discarded or returned to the fiber source. This is typically repeated for each test that is desired. Creating the various samples is time-consuming and somewhat wasteful. While returning the sample to the source generally reduces waste, doing so also tends to increase the amount of time required to perform the test.

Some tests are performed by instruments that have been designed to use a single fiber sample for more than one test. For example, the HVI instrument from Uster Technologies AG of Uster Switzerland takes a single cotton fiber sample and first performs a fiber length measurement and then a fiber strength measurement on the same sample. This tends to reduce the amount of time that is required to perform the testing.

What is needed, therefore, is more integration of testing so as to continue to reduce the number of fiber samples that need to be taken for fiber testing.

SUMMARY

The above and other needs are met by a fiber testing instrument having a fiber loading station that is sized to accommodate a fiber sample within a desired size range, a fiber extraction device for extracting a portion of the fiber sample for a first battery of fiber tests, a fiber transport device for conveying at least the remaining portion of the fiber sample, and a micronaire chamber for receiving the conveyed fiber sample, where the micronaire chamber is sized to test any fiber sample within the desired size range.

DRAWINGS

Further advantages of the invention are apparent by reference to the detailed description when considered in conjunction with the figures, which are not to scale so as to more clearly show the details, wherein like reference numbers indicate like elements throughout the several views, and wherein.

DESCRIPTION

The embodiments described herein are applicable to a wide range of instruments, but are described using the specific example of a fiber micronaire measurement instrument in combination with a fiber length and strength instrument, such as the HVI instrument from Uster Technologies AG of Uster Switzerland.

Figure 1A:
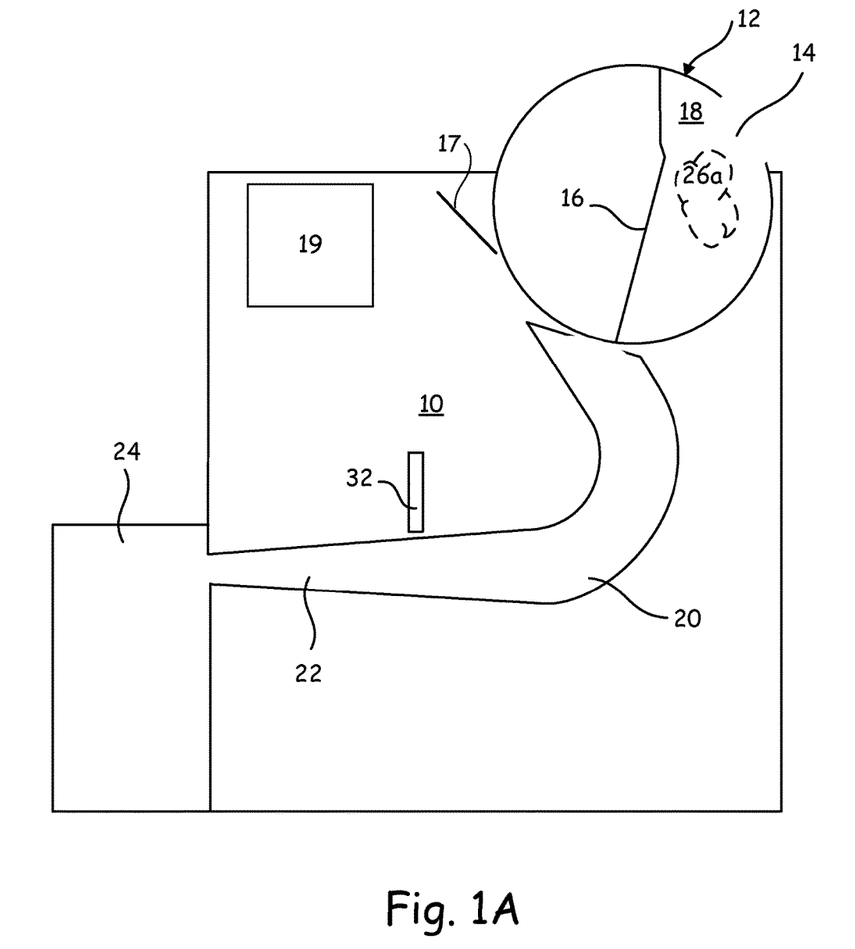
FIG. 1 depicts a fiber sample drum in a fiber sample load position according to an embodiment of the present invention.
Figure 1B:
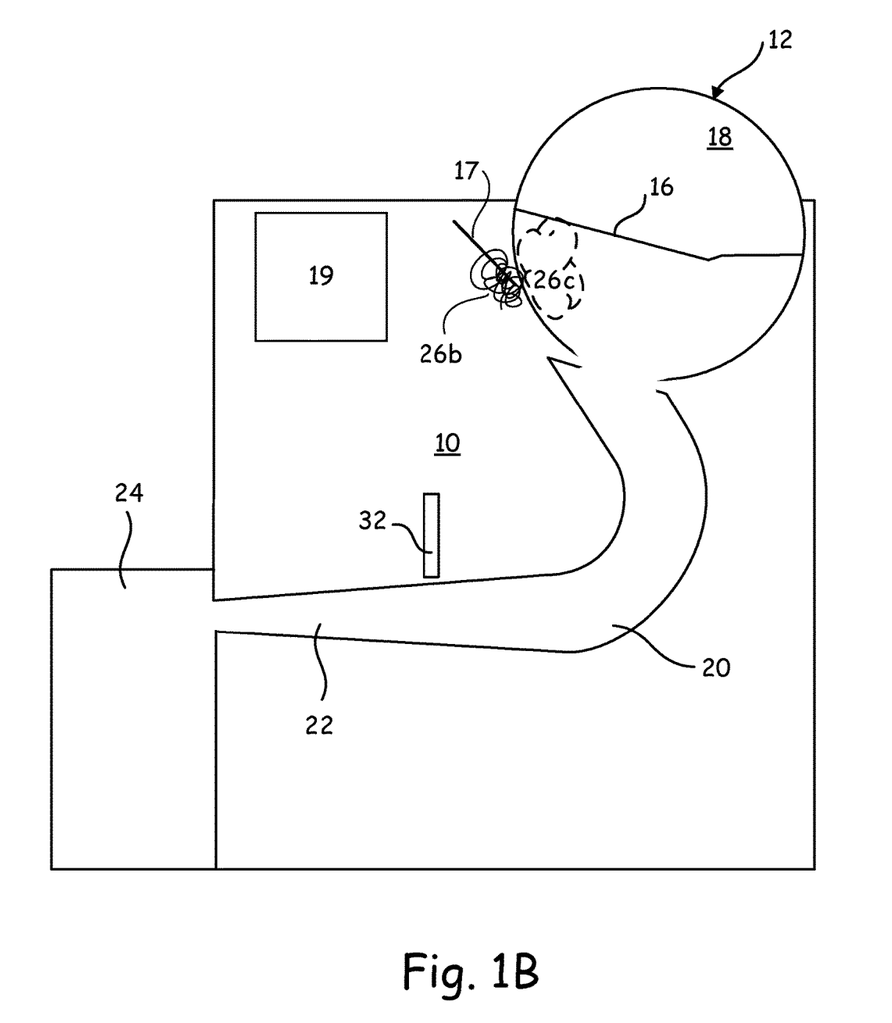
Figure 1C:
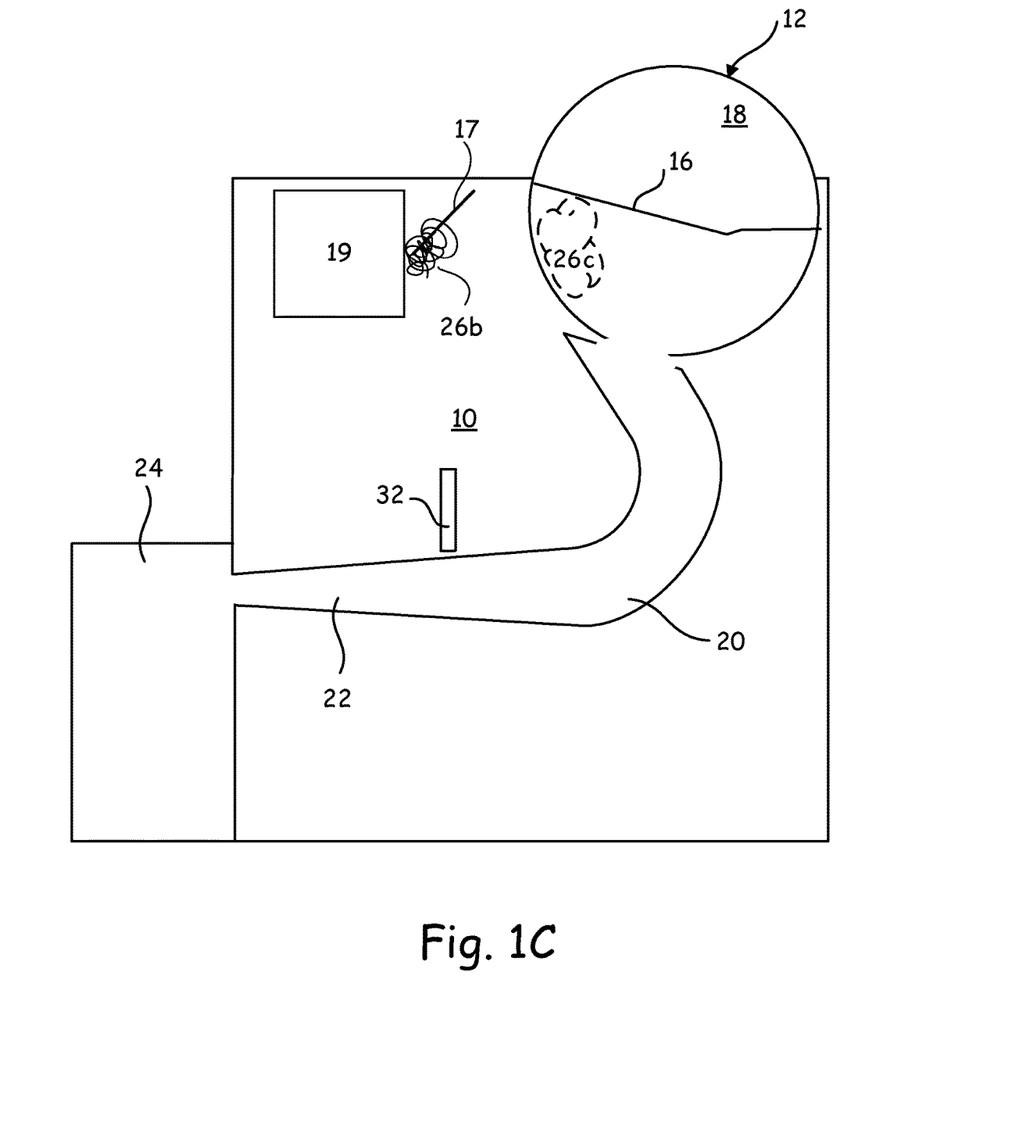

With reference now to FIG. 1, there is depicted an instrument 10 for combined measurement of fiber length, strength, and micronaire. The instrument 10 has a fiber sample receiving station 12, which in the depicted embodiment is configured as a rotating drum. The drum 12 has an opening 14 in the peripheral wall, through which an operator can place a fiber sample 26 into a void 18 in the interior of the drum 12.

The amount of the fiber sample 26 placed in the drum 12 is selected so as to be within a fairly broad range of weights. The operator who loads the fiber sample 26, however, does not weigh the fiber sample 26 that is placed in the drum 12. Instead, the weight range is sufficiently broad that the operator can select a proper fiber sample 26 size merely by judging the amount of fiber that she holds in her hand. Thus, rough visual approximations of the amount of fiber that is held in hand are sufficient to select a fiber sample 26 size that is within the desired weight range.

A mechanism 16 forces the fiber sample 26 against a portion of the peripheral wall of the drum 12 in which apertures have been formed, and press portions of the fiber sample 26 through the apertures such that they protrude outside of the peripheral wall of the drum 12. The drum 12 then rotates. The rotation of the drum 12 passes the protruding fibers past a comb, which extracts some of the fibers from the fiber sample 26. The fibers extracted by the comb are then tested in first battery of tests, such as for length and strength, the operations for which are well known in the art. These fibers are then either discarded or returned to the fiber sample 26, either in the drum 12 or at another point in the process.

Figure 2:
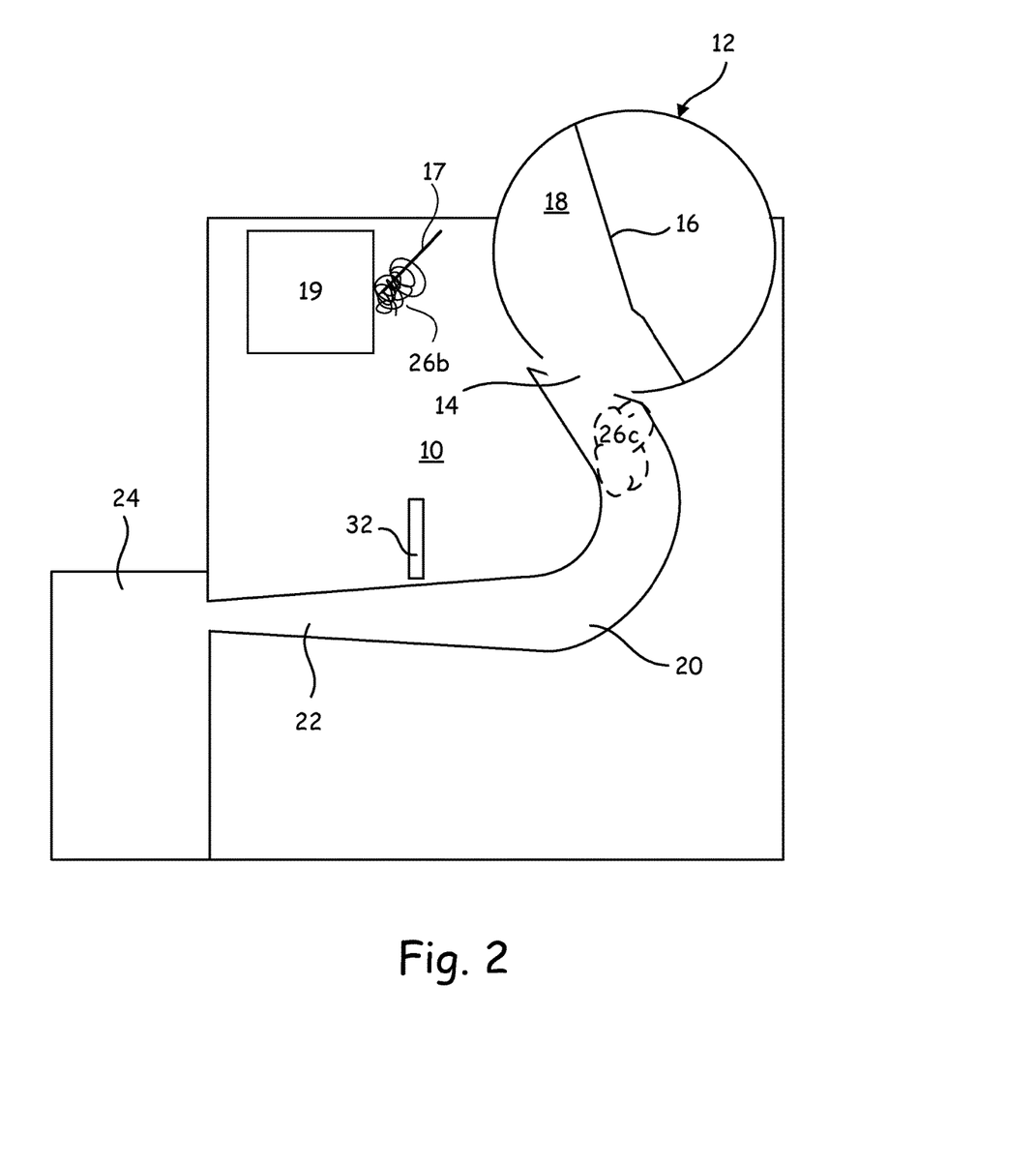
FIG. 2 depicts a fiber sample drum in a fiber sample unload position according to an embodiment of the present invention.

After extracting some of the fibers using the comb, the drum 12 is rotated to a position as depicted in FIG. 2, and the fiber sample 26 within the drum 12 is moved into a transport tube 20. The fiber sample can either be ejected from the drum 12, either mechanically or under pressure, or drawn into the transport tube 20, such as by a vacuum. In one embodiment a venturi 22 creates the vacuum that is used to draw the fiber sample 26 along the transport tube 20, and towards a micronaire measurement instrument 24.

In various embodiments, one or more transport tubes 20 can be disposed to receive fiber samples 26 from one or more drums 12 that are included in the instrument 10. As depicted, the instrument 10 has only one drum 12. However, in other embodiments, the instrument 10 has two or more drums 12. In some embodiments, the fiber samples 26 from any or all of the drums 12 included in the instrument 10 can be transported towards the micronaire instrument 24, using one or more transport tubes 20.

Figure 3:
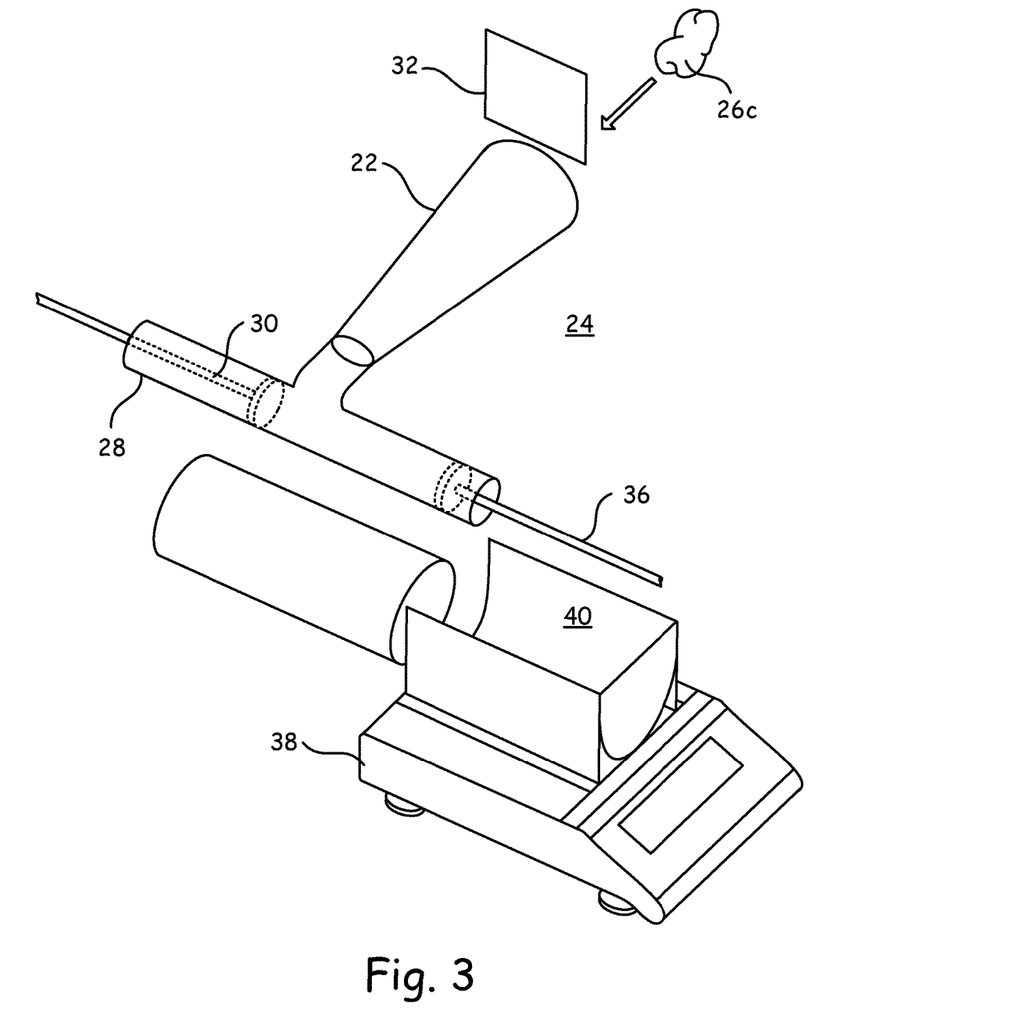
FIG. 3 depicts a micronaire instrument in a fiber sample load position according to an embodiment of the present invention.
Figure 4:
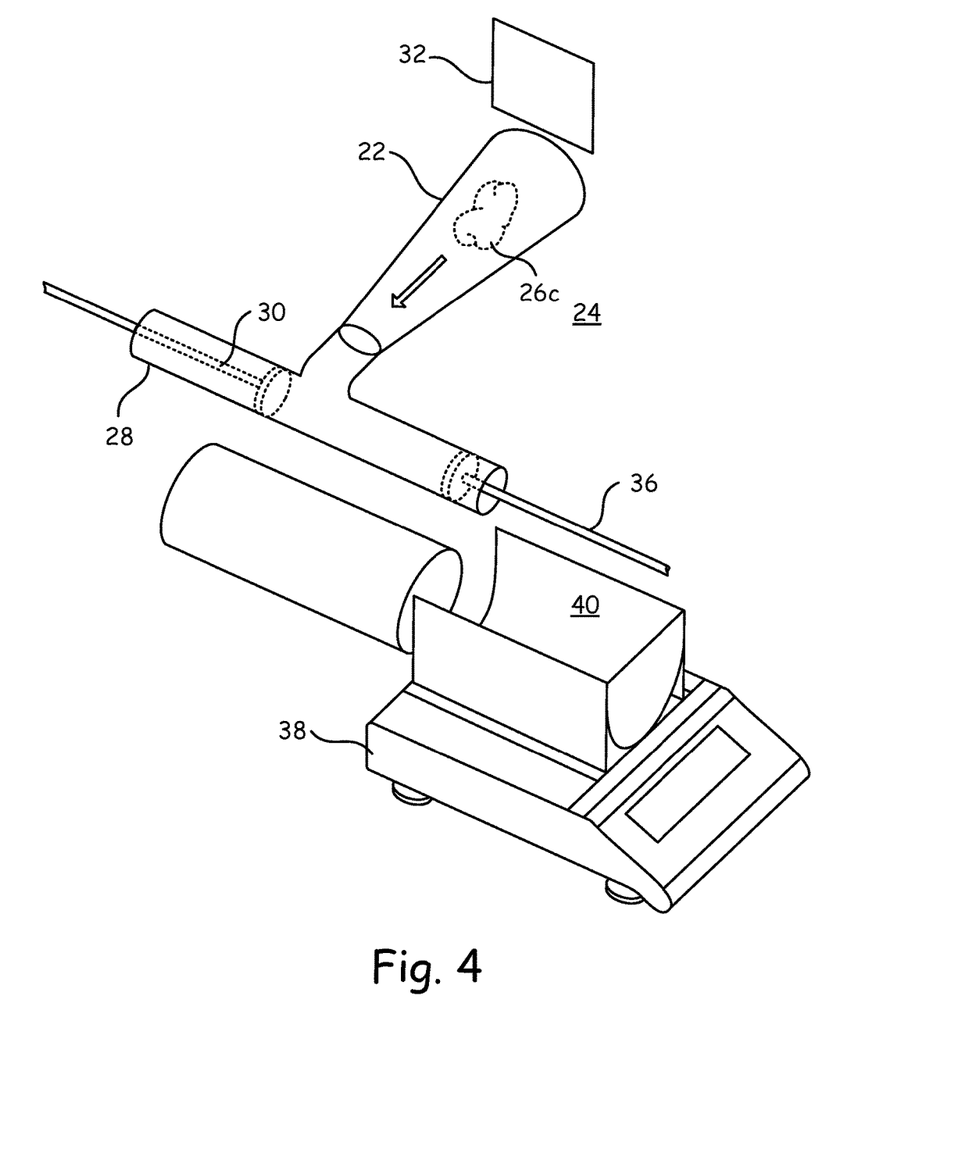
FIG. 4 depicts a micronaire instrument receiving a fiber sample according to an embodiment of the present invention.
Figure 5:
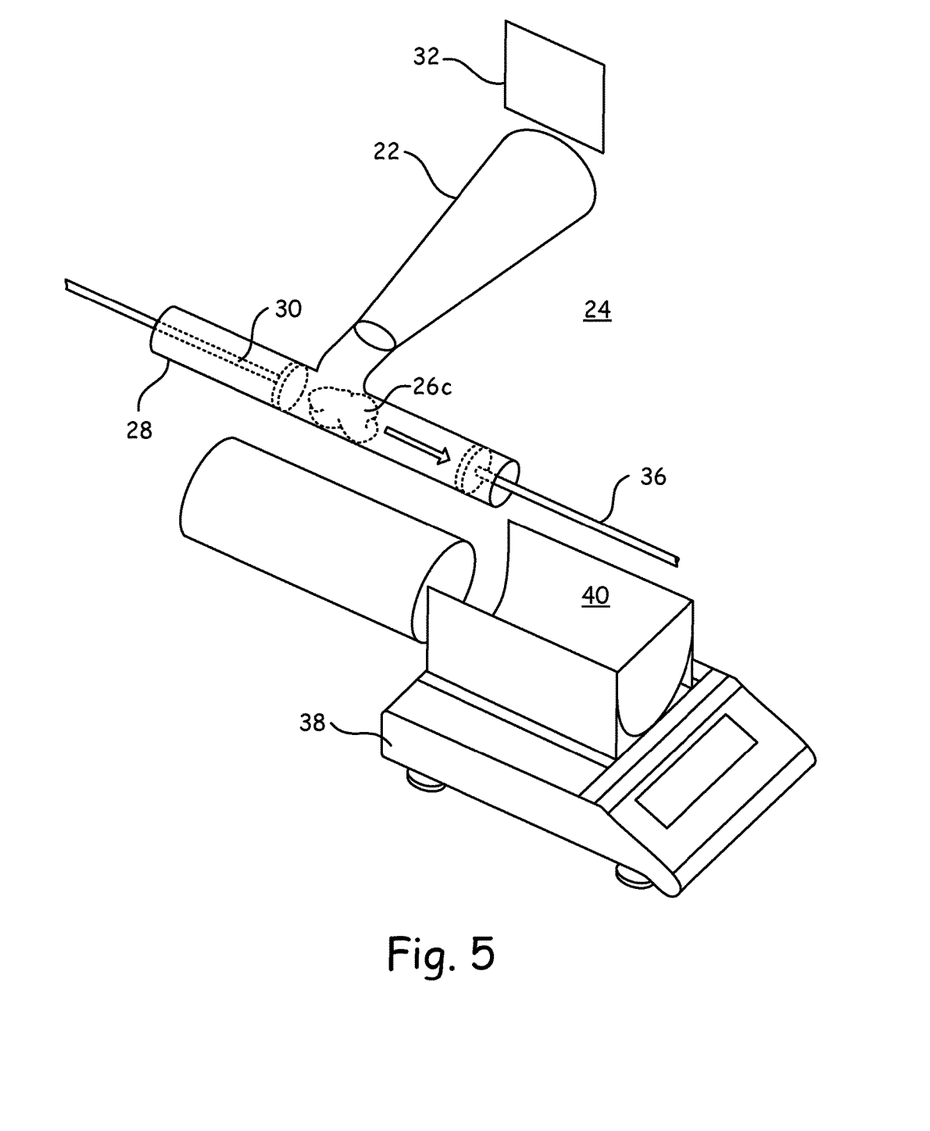
FIG. 5 depicts a micronaire instrument staging a fiber sample in a first position according to an embodiment of the present invention.
Figure 6:
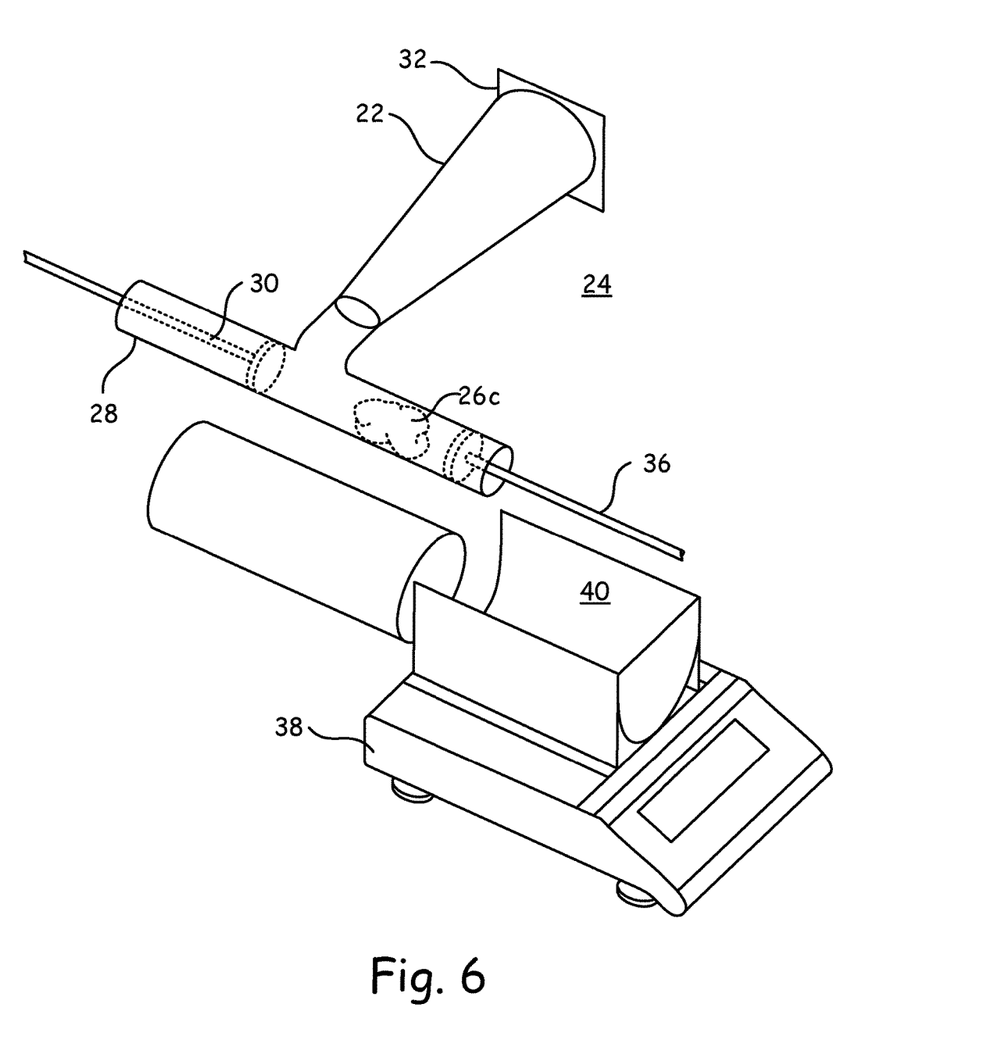
FIG. 6 depicts a micronaire instrument staging a fiber sample in a second position according to an embodiment of the present invention.
Figure 7:
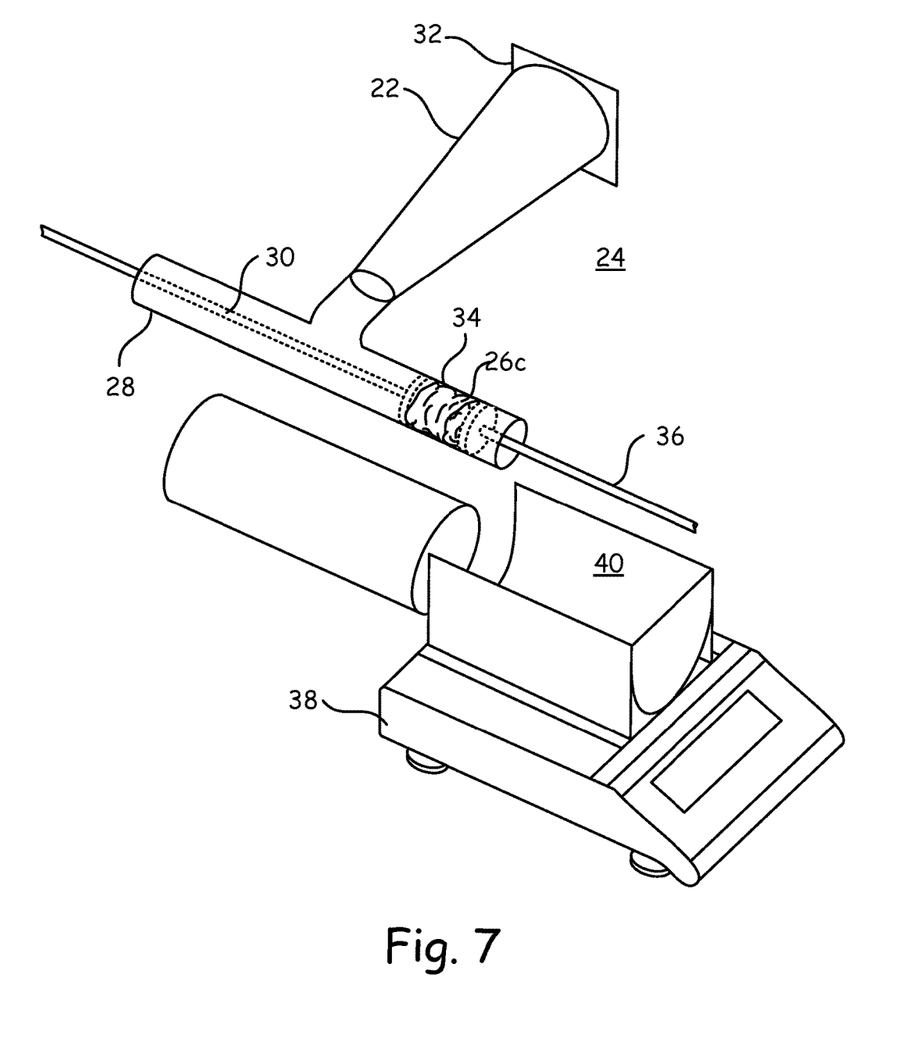
FIG. 7 depicts a micronaire instrument compressing a fiber sample in the micronaire chamber according to an embodiment of the present invention.

With reference now to FIGS. 3 and 4, there are depicted more detailed views of the micronaire 24, the venturi 22, and the fiber sample 26 as it enters the micronaire 24. FIG. 5 depicts the fiber sample 26 after it has passed through the venturi 22 and into the micronaire loading tube 28. After the fiber sample 26 passes out of the transport tube 20, through the venturi 22, and into the loading tube 28, a gate 32 is placed across the transport tube 20, as depicted in FIG. 6. Once the gate 32 is dropped, the venturi 22 naturally produces a pressure that pushes the fiber sample 26 further into the micronaire chamber 34, as depicted in FIG. 7. A rear piston 30 compresses the fiber sample 26 within the micronaire chamber 34 and against an opposing front piston 36. Micronaire measurements are taken on the fiber sample 26, according to methods known in the art.

One benefit of the present embodiments is that the amount of fiber sample 26 that the operator is able to visibly judge in her hand by size or volume is the same amount of fiber sample 26 (less any amount of the fiber sample 26 that was extracted by the comb, if such amount is not returned to the fiber sample 26, such as by being drawn into the transport tube 20 from a different position within the instrument 10) that is tested in the micronaire 24. Normally, the drum sample that feeds the length/strength instrument is selected by size or volume and the Micronaire sample is normally selected by weight or mass. It is unique to use one sample for both a first instrument that typically uses a sample that is selected by size (the drum that feeds the length/strength instrument) and a second instrument that uses a sample that is typically selected by weight (the micronaire 24).

Further, it is novel in the art that a micronaire chamber 34 and a fiber sample receiving drum 12 for a length/strength instrument are sized with respect to one another such that the desired size of the fiber sample 26 is the same for both. In one embodiment, the micronaire chamber 34 is sized so as to receive a fiber sample 26 that is sized for an existing drum 12 size. In another embodiment, the drum 12 is sized to receive a fiber sample 26 that is sized for an existing micronaire chamber 34 size. In either embodiment, correlating the sizes of both the drum 12 and the micronaire chamber 34 has not previously been considered in the art. Neither has using a drum 12 as a common input for the fiber sample 26 for both a first set of tests and a micronaire measurement. Further benefits include the single fiber sample 26 being selected merely by visual inspection in hand.

Figure 8:
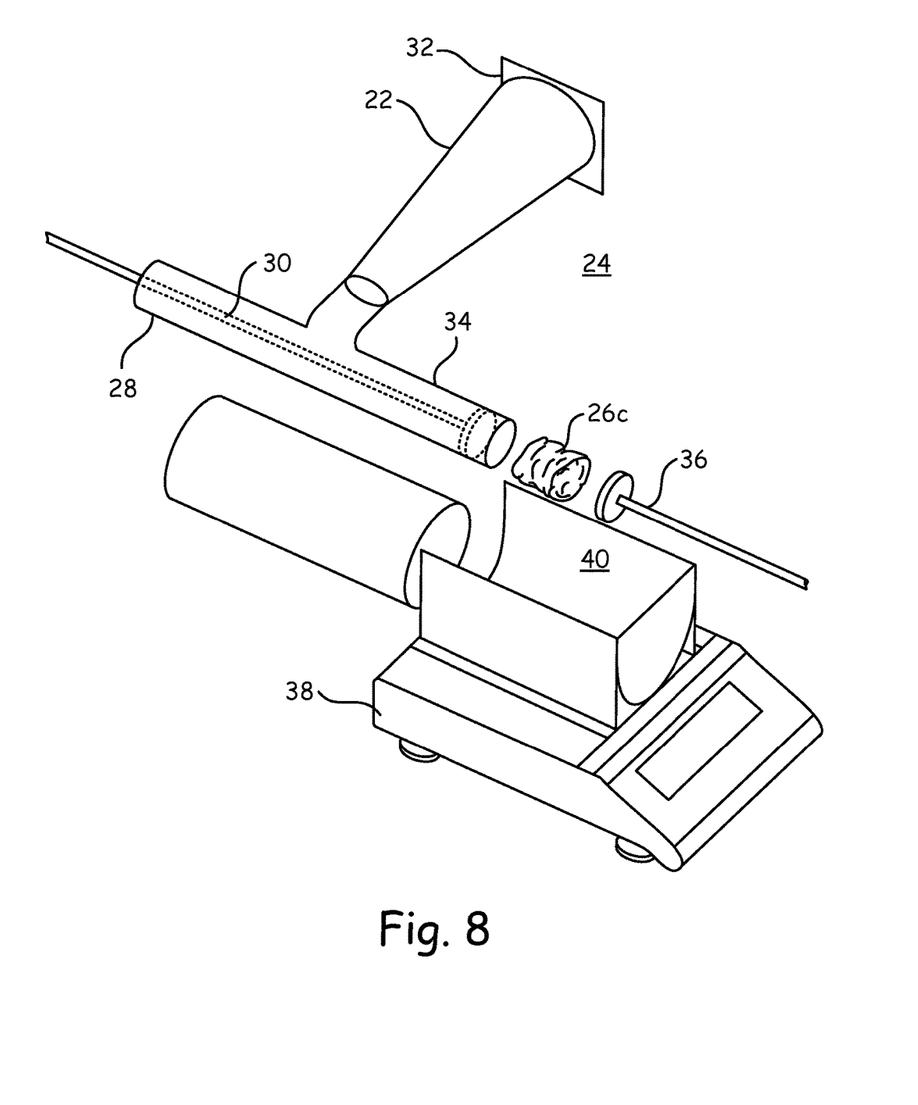
FIG. 8 depicts a micronaire instrument discharging a fiber sample according to an embodiment of the present invention.
Figure 9:
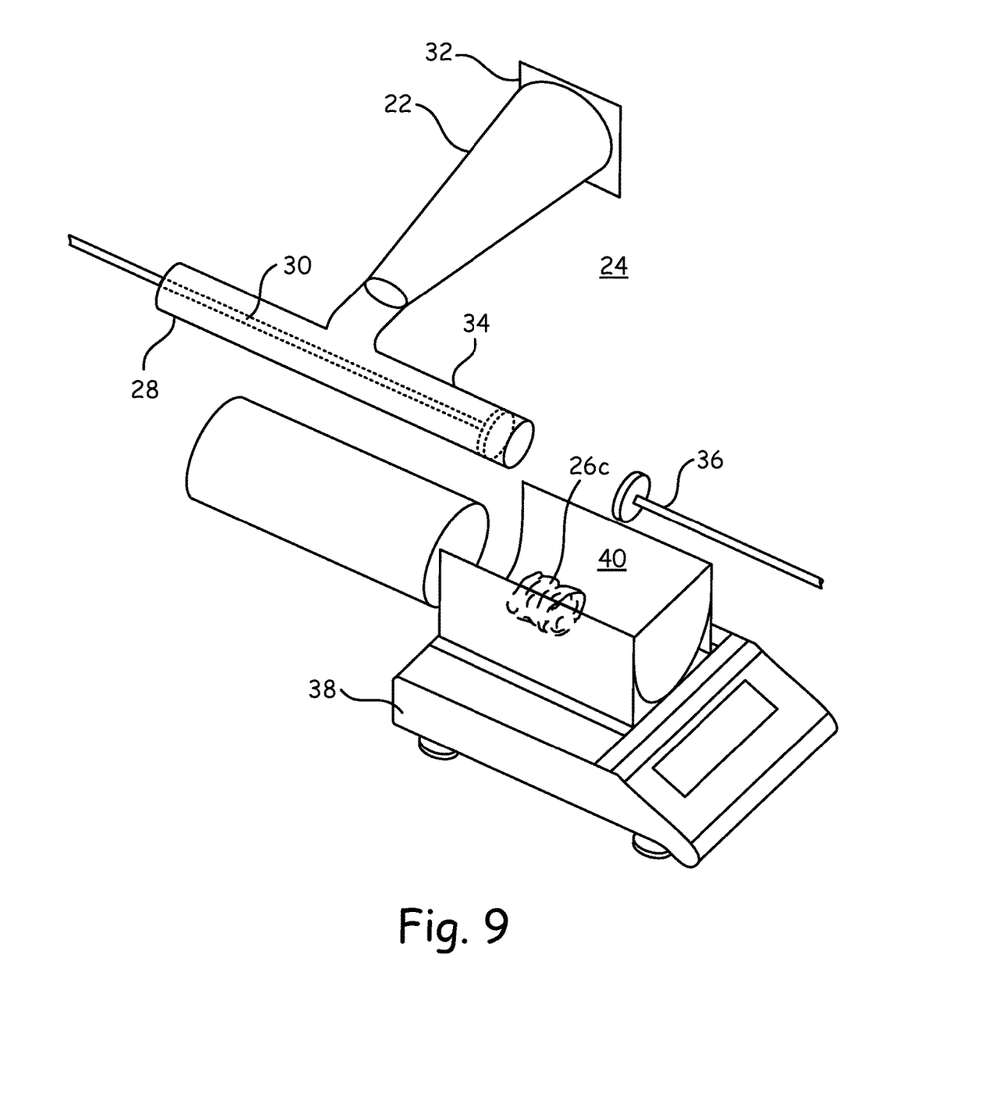
FIG. 9 depicts a scale weighing the fiber sample according to an embodiment of the present invention.
Figure 10:
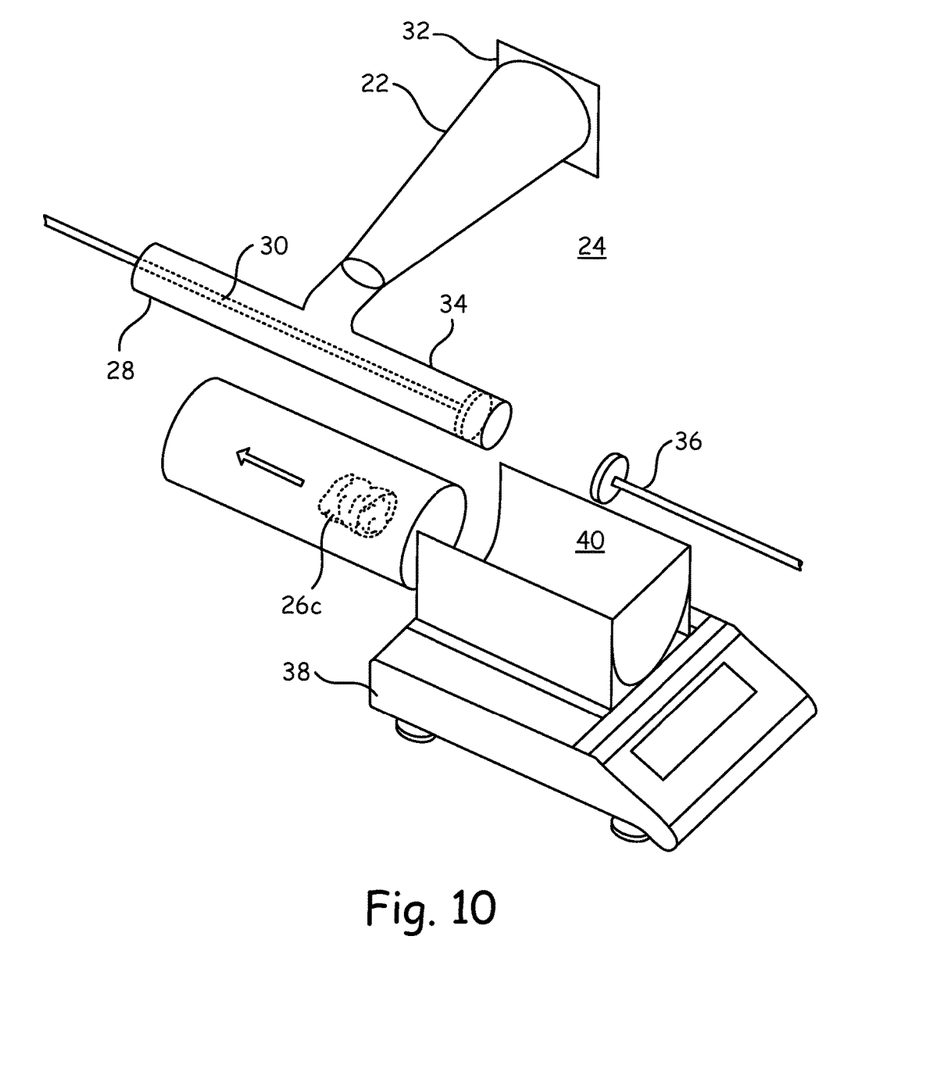
FIG. 10 depicts a fiber sample being discharged from a scale according to an embodiment of the present invention.

After the micronaire measurements have been made, the front piston 36 is withdrawn, the rear piston 30 is extended through the micronaire chamber 34, and the fiber sample 26 falls into a bin 40, as depicted in FIGS. 8 and 9. The bin 40 is, in one embodiment, disposed on a scale 38, and the fiber sample 26 is weighed. The weight of the fiber sample 26 is used to calculate the micronaire of the fiber sample 26, in conjunction with the micronaire measurements that were taken in the chamber 34. However, the acceptable weight range for the micronaire chamber 34 and associated measurements is selected to be compatible with the amount of the fiber sample 26 that the operator judges in her hand and places within the drum 12 for all of the testing. Once the weight of the fiber sample 26 has been read, the fiber sample 26 can be ejected or otherwise withdrawn from the micronaire 24, as depicted in FIG. 10. The fiber sample 26 is, in some embodiments, either discarded or returned to the fiber source from which it was originally extracted by the operator.

In some embodiments a single control panel on the instrument 10 provides for control input to and measurement output from the first battery of tests, the transport mechanism, and the micronaire test.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of testing fibers, comprising:
receiving a multiple fiber sample with a fiber loading station, where the fiber loading station can hold no more than a maximum weight of fibers in the sample,
performing a first set of fiber tests on a multiple fiber extracted portion of the fiber sample with a first testing module, thereby leaving a multiple fiber remaining portion within the fiber loading station, where the remaining portion has no less than a minimum weight,
conveying with a transport device the remaining portion from the fiber loading station to a second testing module that is sized to accommodate any fiber weight between the minimum weight and the maximum weight, and
performing micronaire testing on the remaining portion with the second testing module.

2. The method of claim 1, wherein the fiber loading station is a drum.

3. The method of claim 1, wherein the fiber transport device is an air flow provided by a venturi within a conduit.

4. The method of claim 1, wherein the first set of fiber tests includes at least one of fiber length and fiber strength.

5. A fiber testing instrument comprising:
a fiber loading station sized to hold no more than a maximum sample weight of a multiple fiber starting fiber sample, wherein the fiber loading station is a drum,
a fiber extraction device for extracting from the fiber loading station a portion of the starting fiber sample, thereby producing an extracted portion of multiple fibers, and a remaining portion of multiple fibers inside the fiber loading station that is no less than a minimum sample weight, a first testing module for performing a first set of fiber tests on the extracted portion, a fiber transport device for conveying all of the remaining portion from the fiber loading station to a micronaire chamber, and the micronaire chamber for receiving all of the remaining portion from the fiber transport device, which micronaire chamber is sized to test micronaire of any weight of fibers between the minimum sample weight and the maximum sample weight.

6. The fiber testing instrument of claim 5, wherein the first set of fiber tests includes at least one of fiber length and fiber strength.

7. The fiber testing instrument of claim 5, wherein the fiber transport device comprises a conduit flowed through with an air flow generated by an air-operated vacuum pump.

* * * * *